(12) United States Patent
Cutler et al.

(10) Patent No.: US 6,251,832 B1
(45) Date of Patent: Jun. 26, 2001

(54) FUNGICIDE COMPRISING 4-METHYL-6-PENTYL-2H-PYRAN-2-ONE

(76) Inventors: Horace G. Cutler, 1050 Hollow Creek Run, Watkinsville, GA (US) 30677; Stephen R. Parker, 62A Upland Road., Kelburn, Wellington (NZ); Robert A. Hill, 54 Gordonton Road, Taupiri 2171 (NZ)

(*) Notice: Subject to any disclaimer, the term of this patent is extended or adjusted under 35 U.S.C. 154(b) by 0 days.

(21) Appl. No.: 09/486,268

(22) PCT Filed: Jan. 21, 2000

(86) PCT No.: PCT/NZ98/00108

§ 371 Date: Feb. 24, 2000

§ 102(e) Date: Feb. 24, 2000

(87) PCT Pub. No.: WO99/04633

PCT Pub. Date: Feb. 4, 1999

(30) Foreign Application Priority Data

Jul. 21, 1997 (NZ) .................................................... 328382

(51) Int. Cl.[7] ...................................................... A01N 43/16

(52) U.S. Cl. ............................................. 504/292; 514/460

(58) Field of Search ............................... 504/292; 514/460

(56) References Cited

FOREIGN PATENT DOCUMENTS

WO9904633    4/1999   (WO) .

OTHER PUBLICATIONS

Pittit, AO et al 'Synthesis and flavor properties of some alkyl–substituted alpha–pyrone derivatives' CA 83;191473, 1975.*

* cited by examiner

*Primary Examiner*—Amelia Owens
(74) *Attorney, Agent, or Firm*—Roylance, Abrams, Berdo & Goodman, L.L.P.

(57) ABSTRACT

The invention provides a fungicidal composition comprising the compound 4-methyl-6-pentyl-2H-pyran-2-one and one or more suitable carriers, adjuvants and/or diluents. Also provided is a method of preventing or at least inhibiting the growth of fungi which comprises the step of applying the compound of the fungi or their locus. Further provided is a process for preparing the compounds.

9 Claims, 3 Drawing Sheets

I

II

III

IV

V

VI

FUNGICIDE COMPRISING 4-METHYL-6-PENTYL-2H-PYRAN-2-ONE

FIELD OF THE INVENTION

The present invention is directed to a compound having fungicidal activity, to fungicidal compositions containing the compound, and to methods of using them.

BACKGROUND ART

The antifungal activity of the natural product 6-pentyl-2H-pyran-2-one (6-PAP) is well known and the in vitro activity of this compound against a range of phytopathogens has been reported (1, 2, 3, 4). Early structure-activity studies indicated that minor structural modifications to 6-PAP yielded compounds with reduced antifungal activity (5).

Prior to its identification as a natural product, the chemical synthesis of 6-PAP and its structural analogs received attention because of the potent organoleptic properties of these compounds (6, 7). However, despite the attention paid to the synthesis of 6-PAP by these and other methods (8, 9), its preparation remains costly.

As an organic natural product 6-PAP is innately biodegradable. Combined with its established use as a food additive and assumed low toxicity 6-PAP is an attractive candidate for development as an agricultural/horticultural fungicide. However, its cost is an obstacle to further development.

The applicants have now surprisingly found that a structural analog of 6-PAP, namely 4-methyl-6-pentyl-2H-pyran-2-one, has fungicidal activity similar to that of compound 6PAP. The applicants have also found that 4-methyl-6-pentyl-2H-pyran-2-one can be prepared with relative ease and economy as compared to preparation of 6-PAP. It is towards the use of 4-methyl-6-pentyl-2H-pyran-2-one as a fungicide that the present invention is directed.

SUMMARY OF THE INVENTION

Accordingly, in a first aspect, the present invention provides a fungicidal composition comprising the compound 4-methyl-6-pentyl-2H-pyran-2-one, in combination with one or more suitable carriers, adjuvants and/or diluents.

In a second aspect, the present invention provides a method of preventing or at least inhibiting the growth of fungi which comprises the step of applying the compound 4-methyl-6pentyl-2H-pyran-2-one to the fungi or their locus.

In a third aspect, the present invention provides a method of preparing the compound 4-methyl-6-pentyl-2H-pyran-2-one, the method comprising the following steps:

(a) reacting the compound ethyl 3-methyl-2-butenoate with hexanoyl chloride under suitable conditions to produce Friedel-Crafts acylation products; and (b) reacting the acylation products obtained in step (a) with a concentrated acid under conditions suitable to achieve lactonisation and thereby obtain the compound 4-methyl-6-pentyl-2H-pyran-2-one.

Those persons skilled in the art will appreciate that although the invention is broadly defined above, it also includes embodiments of which the following description provides examples.

DESCRIPTION OF THE DRAWINGS

Various aspects of the invention are also illustrated in the accompanying drawings in which.

DETAILED DESCRIPTION OF THE INVENTION

Figure 1:
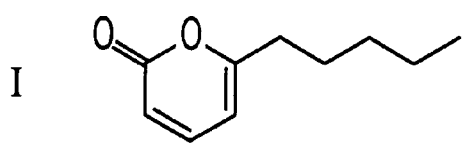
FIG. 1 shows structures of various pyrone analogs which were tested for antifungal activity, including the compound of the present invention (compound II) and 6-PAP (compound I)
Figure 1:
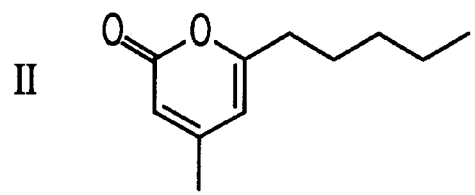
Figure 1:
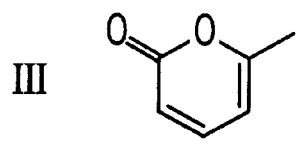
Figure 1:
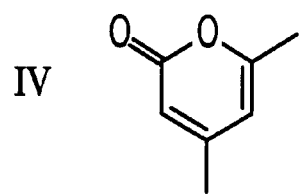
Figure 1:
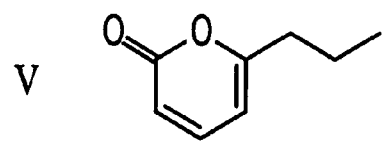
Figure 1:
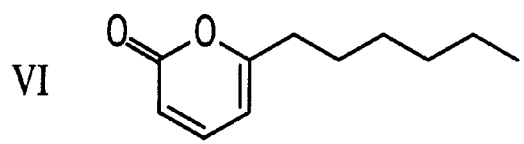
Figure 1:
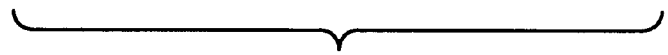

As defined above, the invention is generally directed to the compound 4-methyl-6-pentyl-2H-pyran-2-one. This compound has been unexpectedly found by the applicants to have fungicidal properties.

The compound can be prepared using the following synthetic route:

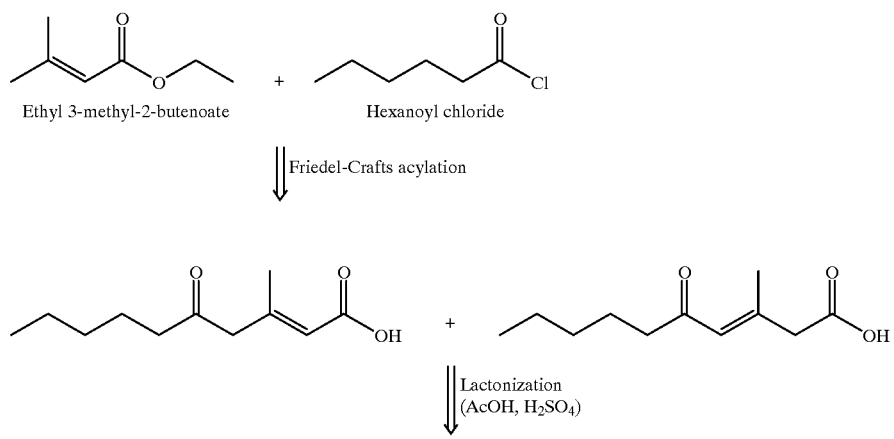

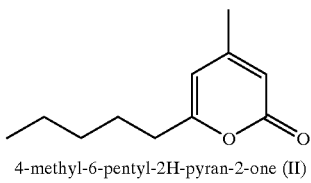

4-methyl-6-pentyl-2H-pyran-2-one (II)

ie. by Friedel-Crafts acylation of ethyl 3-methyl-2-butenoate with hexanoyl chloride to produce mixed keto-acids, followed by lactonization of the mixed keto-acids using a suitable concentrated acid (conveniently a mixture of glacial acetic acid and concentrated sulphuric acid).

The starting material for the above synthetic route, namely ethyl 3-methyl-2-butenoate, is able to be prepared quantitatively and relatively cheaply, by esterification of 3,3-dimethylacrylic acid. This enables the compound 4-methyl-6-pentyl-2H-pyran-2-one to be prepared relatively economically and easily, as compared to 6-PAP.

The present invention also includes fungicidal compositions comprising the compound 4-methyl-6-pentyl2H-pyran2-one, in combination with one or more suitable carriers, adjuvants or diluents. It is believed that the compound of the invention will prove particularly suitable as an agricultural or horticultural fungicide. As such, suitable carriers or diluents will be apparent to those persons skilled in the art.

In use, the compositions can be applied either directly to fungi or to their locus to prevent or inhibit the growth of the fungi. For example, the compositions can be applied to the foliage of vegetables and plants, to seeds or to soil surrounding plants.

EXPERIMENTAL

Structure of compounds tested:

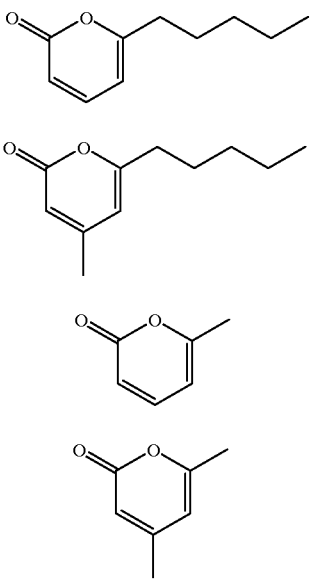

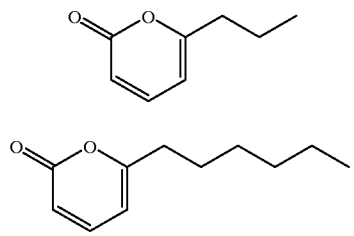

Preparation of 4-Methyl-6-Pentyl-2H-Pyran-2-One

Ten grams 3,3-dimethylacrylic acid was dissolved in 100 ml absolute ethanol and 0.5 ml concentrated (37% approx.) hydrochloric acid added. The reaction mix was refluxed for 24 to 48 hours with a Dean-Stark trap filled with activated molecular sieves inserted between the reaction vessel and the condenser. After cooling, the solvent was removed by rotary evaporation under reduced pressure at 50° C. to yield 6.3 g of a cloudy, yellow oil (ethyl 3-methyl-2-butenoate.)

Ethyl 3-methyl-2-butenoate (6.3 g) was added dropwise with 6.7 g of hexanoyl chloride at ambient temperature to a stirred, suspension of 6.6 g aluminium chloride in 30 ml dry methylene chloride. The resulting orange-brown reaction mix was refluxed for three hours. After cooling a further 30 ml methylene chloride was added to the reaction mix and the whole poured over a crushed ice-water mix. The two phase mixture was allowed to stand and the lower, organic phase collected. The aqueous phase was extracted twice with methylene chloride and the pooled extracts washed with a saturated sodium bicarbonate solution and allowed to stand overnight. The organic layer was collected, dried over anhydrous sodium sulphate and reduced by rotary evaporation to yield 8.7 g of a dark brown oil (mixed keto acids.)

Figure 4:
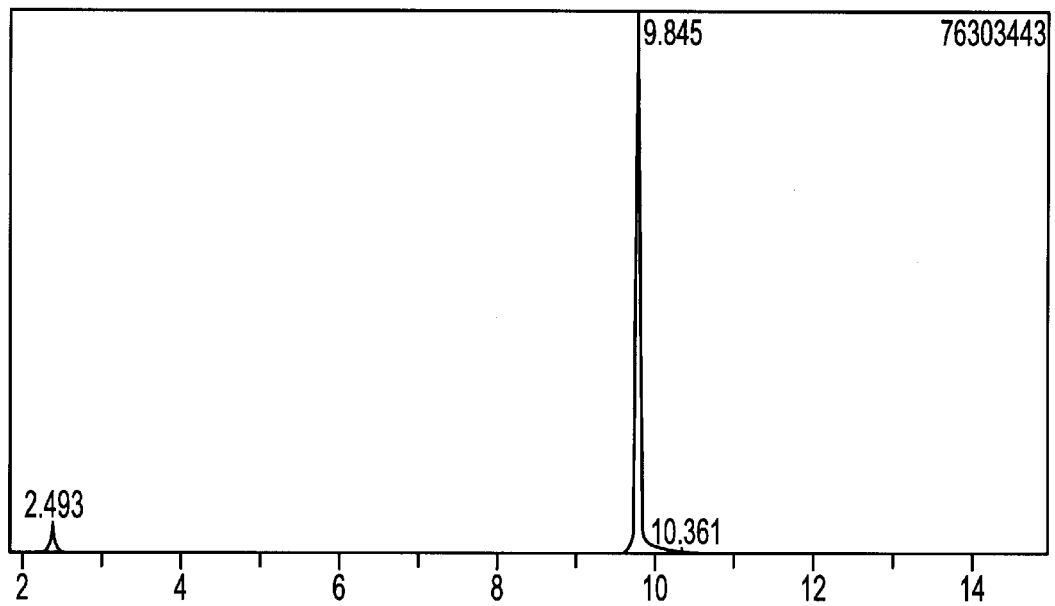
FIGS. 4 and 5 show a gas chromatographic and mass spectral analysis of 4-methyl-6-pentyl-2H-pyran-2-one.
Figure 5:
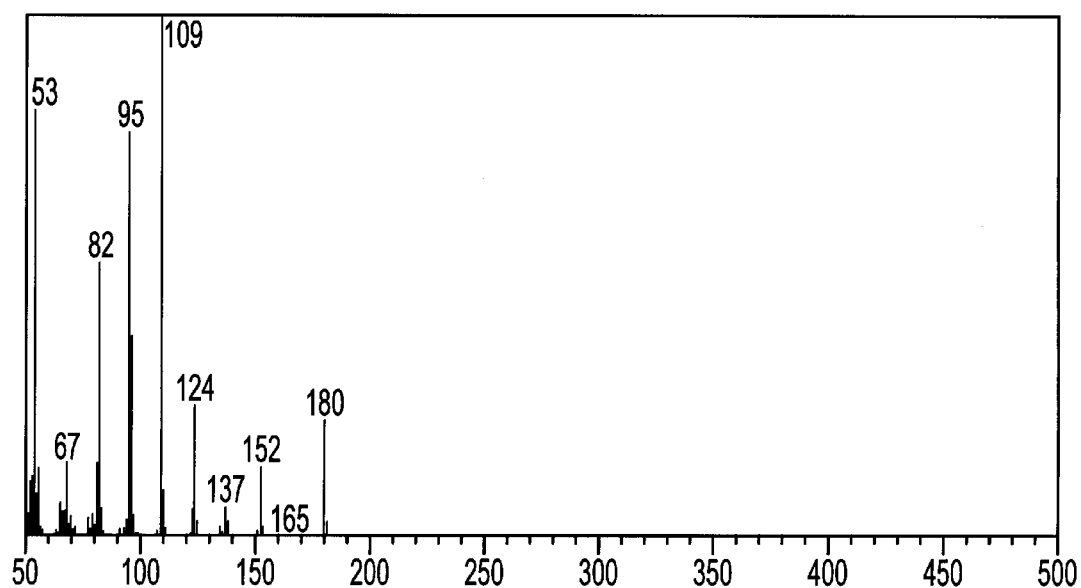

For lactonisation 8.7 g of the mixed keto acids were dissolved in 30 ml glacial acetic acid and 1 ml concentrated sulphuric acid added. The mixture was refluxed for 30 minutes, cooled and poured over a crushed ice-water mixture. The aqueous volume was extracted with hexane, the pooled hexane extracts dried over anhydrous sodium sulphate and finally reduced by rotary evaporation to yield 3.5 g of crude product. 4-Methyl-6-pentyl-2H-pyran-2-one was purified from the crude product by fractional vacuum distillation at c. −75 cmHg and distilled between 170 and 200° C. The identity of the product was confirmed by GC-MS (FIGS. 4 and 5).

Antifungal Activity—Agar Diffusion Assay

Spore suspensions were prepared by washing sporulating plates or slopes of the test organism with 10 ml sterile 0.1% (v/v) Tween 80. The spore density of the aspirated volume was determined using an improved Neubauer haemocytometer. The spore suspension was used to inoculate molten potato dextrose agar (PDA) maintained at 45° C. Ten milliliters of the inoculated PDA was poured over the surface of a petri dish (90 mm dia.) containing a uniform base layer of 10 ml 1% (w/v) water agar and allowed to solidify.

Solutions of test compounds were prepared in acetone and applied to sterile 6 mm diameter filter paper discs (Whatman no. 3.) After allowing the solvent to evaporate impregnated filter paper discs were placed on the surface of the solidified agar. Three discs were used per plate placed equidistant from each other and the centre of the plate. Plates were incubated at 25° C. for 24 hours and the diameters of the resulting zones of inhibition measured.

Results

Figure 2:
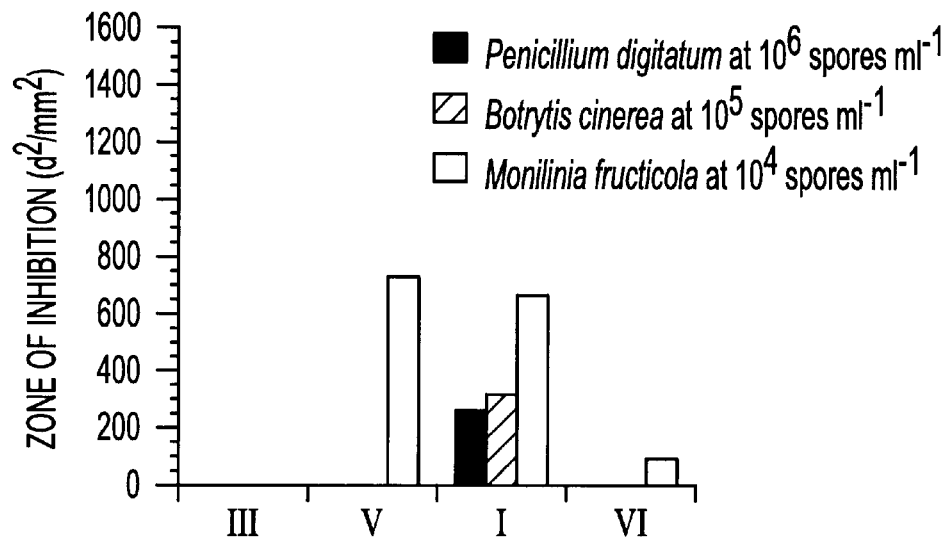
FIG. 2 shows results of tests of antifungal activity of compounds I, III, V and VI of FIG. 1.
Figure 3:
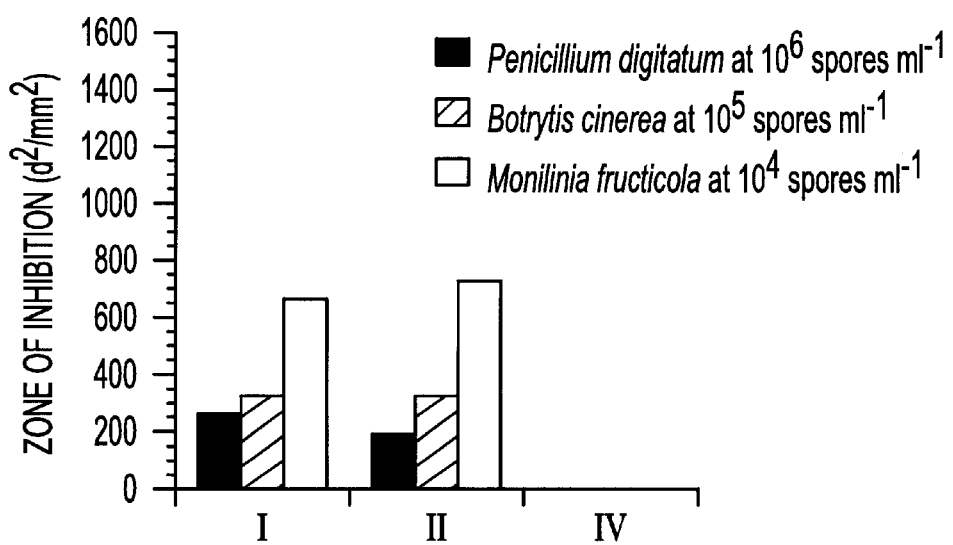
FIG. 3 shows results of tests of antifungal activity of compounds I, II and IV of FIG. 1.

Minor modifications to the structure of 6-PAP have previously been demonstrated to yield compounds with significantly reduced in vitro antifungal activity. This is confirmed and illustrated here for the compounds III, V and VI (FIG. 2). By contrast 4-methyl-6-pentyl-2H-pyran-2-one retains activity similar to that of 6PAP (FIG. 3). This is particularly striking in light of the fact that the magnitude of the structural modification; addition of a single methyl unit, is the same for 4-methyl-6-pentyl-2H-pyran-2-one (active) and compound VI (inactive.) This observation is fortuitous when the relative ease and economy of the preparation of 4-methyl-6-pentyl-2H-pyran-2-one is compared with that of 6-PAP. It should also be noted that the presence of a 6-pentyl substituent is critical to the activity of 4-methyl-6-pentyl-2H-pyran-2-one (of compound IV.)

INDUSTRIAL APPLICABILITY

As will be apparent from the above experimental data, the applicants have found that compound 4-methyl-6-pentyl-2H-pyran-2-one has a similar level and spectrum of in vitro antifungal activity to 6-PAP. This is surprising, particularly since the other analogs of 6-PAP tested (compounds III–VI) showed either no activity or significantly reduced activity compared to 6-PAP.

It is believed that the compound of the invention will find acceptance as a fungicide, and in particular as a fungicide for use in agricultural and horticultural applications.

It will be appreciated that the above description is provided by way of example only and that variations and modifications will be apparent to those persons skilled in the art without departing from the scope of the following claims.

REFERENCES

1. Cutler, H. G., *Biologically Active Natural Products Prom Fungi: Templates for Tomorrow's Pesticides*, in *Bioregulators, Chemistry and Uses*, R. L. Ory and F. R. Rittig, Editors. 1984, American Chemical Society: Washington, D.C.

2. Cutler, H. G., et al., *6-Pentyl-a-pyrone from Trichoderma harzianum: Its Plant Growth Inhibitory and Antimicrobial Properties*. Agricultural and Biological Chemistry, 1986. 50(11): p 2943–2945.

3. Claydon, N., et al., *Antifungal Alkyl Pyrones of Trichoderma harzianum*. Transactions of the British Mycological Society, 1987. 88(4): p 503–513.

4. Scarselletti, R. and J. L. Faull, *In vitro activity of 6-pentyl-a-pyrone, a metabolite of Trichoderma harzianum, in the inhibition of Rhizoctonia solani and Fusarium oxysporum f. sp. lycopersici*. Mycol. Res., 1994. 98(10): p 1207–1209.

5. Dickinson, J. M. 1988, D. Phil. thesis, University of Sussex.

6. Nobuhara, A., *Syntheses of Unsaturated Lactones. Part 1. Some lactones of 5-substituted-5-hydroxy-2-enoic acids as a synthetic butter or butter cake flavor*. Agr. Biol. Chem., 1968. 32(8): p 1016–1020.

7. Pittet, A. O. and E. M. Klaiber, *Synthesis and flavor properties of some alkyl-substituted a-pyrone derivatives*. J. Agric. Food Chem., 1975. 23(6): p 1189–1195.

8. Dieter, R. K. and J. R. Fishpaugh, *Synthesis of a-pyrones from vinylogous thiol esters and a-oxo ketene dithioacetals*. J. Org. Chem., 1988. 53: p 2031–2046.

9. Zhang, C., et al., *A facile total synthesis of 6-pentyl-a-pyrone*. Chin. Chem. Lett., 1996. 7(4): p 317–318.

What is claimed is:

1. A fungicidal composition comprising the compound 4-methyl-6-pentyl-2H-pyran-2-one in combination with one or more suitable carriers, adjuvants and/or diluents.

2. A fungicidal composition as claimed in claim 1 which is suitable for agricultural or horticultural use.

3. A method of preventing or at least inhibiting the growth of fungi which comprises the step of applying the compound 4-methyl-6-pentyl-2H-pyran-2-one to the fungi or to their locus.

4. A method as claimed in claim 3 wherein the compound 4-methyl-6-pentyl-2H-pyran-2-one is applied in the form of a fungicidal composition as claimed in claim 1 or claim 2.

5. A method as claimed in claim 3 or claim 4 wherein the application of the compound is to the foliage of plants, to soil surrounding plants or to seeds.

6. A composition according to claim 1 wherein said 4-methyl-6-pentyl-2H-pyran-2-one has been made acylation and lactonization of ethyl 3-methyl-2-butanoate.

7. A method according to claim 3 wherein said compound is applied to plant foliage.

8. A method according to claim 3 wherein said compound is applied to soil.

9. A method according to claim 3 wherein said compound is applied to seeds.

* * * * *